United States Patent
Sutich

(10) Patent No.: US 9,987,304 B2
(45) Date of Patent: Jun. 5, 2018

(54) METHOD AND TOPICAL COMPOSITION FOR THE TREATMENT OF ROSACEA AND SKIN ERYTHEMA USING SELENIUM SULFIDE

(71) Applicant: Paul Sutich, Long Branch, NJ (US)

(72) Inventor: Paul Sutich, Long Branch, NJ (US)

( * ) Notice: Subject to any disclaimer, the term of this patent is extended or adjusted under 35 U.S.C. 154(b) by 0 days. days.

(21) Appl. No.: 15/397,150

(22) Filed: Jan. 3, 2017

(65) Prior Publication Data

US 2017/0112873 A1   Apr. 27, 2017

(51) Int. Cl.
| | | |
|---|---|---|
| *A61K 33/04* | (2006.01) |
| *A61K 9/00* | (2006.01) |
| *A61K 9/06* | (2006.01) |
| *A61K 47/46* | (2006.01) |
| *A61K 47/44* | (2017.01) |

(52) U.S. Cl.
  CPC .......... *A61K 33/04* (2013.01); *A61K 9/0014* (2013.01); *A61K 9/06* (2013.01); *A61K 47/44* (2013.01); *A61K 47/46* (2013.01)

(58) Field of Classification Search
  CPC ........ A61K 9/0014; A61K 9/06; A61K 33/04; A61K 47/44; A61K 47/46
  See application file for complete search history.

(56) References Cited

U.S. PATENT DOCUMENTS

2002/0164381 A1* 11/2002 Shacknai ............... A61K 9/143
  424/689
2009/0068128 A1*  3/2009 Waddington ........... A61K 8/673
  424/59

* cited by examiner

*Primary Examiner* — Michael B. Pallay
(74) *Attorney, Agent, or Firm* — Charles I Brodsky

(57) ABSTRACT

A method for the treatment of facial Rosacea and skin erythema using selenium sulfide as the sole active ingredient in a topically applied administration to a user's face in combination with an inactive moisturizing ingredient.

6 Claims, No Drawings

METHOD AND TOPICAL COMPOSITION FOR THE TREATMENT OF ROSACEA AND SKIN ERYTHEMA USING SELENIUM SULFIDE

CROSS-REFERENCE TO RELATED APPLICATIONS

None.

STATEMENT REGARDING FEDERALLY SPONSORED RESEARCH OR DEVELOPMENT

None.

REFERENCE TO A MICROFICHE APPENDIX

None.

BACKGROUND OF THE INVENTION

Field of the Invention

This invention relates to the treatment of Rosacea and skin erythema, in general, and to a method utilizing a topical composition employing selenium sulfide of different concentrations depending on the severity and extent of user symptoms, in particular.

Description of the Related Art

Rosacea is a very common red, acne-like benign skin condition that affects approximately 45 million people worldwide. Its main symptoms include red or pink facial skin, small dilated blood vessels, small red bumps sometimes containing pus, cysts, and pink or irritated eyes. Characteristically involving the central region of the face (mainly the forehead, the cheeks, the chin, and the lower half of the nose), Rosacea is considered a chronic, long-term incurable skin condition with periodic ups and downs. Tending to occur more frequently in women, but more severely in men, Rosacea strikes both at potentially all ages. Unfortunately, emotional factors such stress, fear, anxiety and embarrassment have been determined to aggravate the condition.

While lacking evidence that Rosacea can be spread by contact with the skin, the sharing of towels, or through inhalation, left untreated, the condition tends to worsen over time. Often being mistaken for acne, an allergic reaction, or other skin problems, its signs and symptoms may flair up for a period of weeks to months, and then diminish before flaring up again. Often aggravated by flushing, the redness in Rosacea may cause small blood vessels in the face to enlarge permanently and become more visible through the skin, appearing like tiny red lines. Continual or repeated episodes of flushing and blushing may promote inflammation, causing small red bumps often resembling teenage acne.

While not considered contagious or infectious—and even not necessarily requiring treatment if the individual is not bothered by the condition—many treatment choices are available depending on the severity and extent of symptoms. Antibacterial washes, topical medications, oral antibiotics, lasers, pulsed-light therapies, photodynamic therapy, and isotretinoin have oftentimes been utilized—with varying degrees of success and commensurate costs. Combination uses of them are not uncommon, with some being utilized alternatingly in the morning and at night, and others, such as with topical medications, more than once or twice a day. With metronidazole topical antibiotic medication (Rosadan®) and Azelaic Acid (Finacea®) costing in prescription amounts by dermatologists of $300.00 and more, it would be advantageous to have a simple pharmaceutical composition to effectively overcome the flushing and redness in the case of facial Rosacea, which is not yet achievable by the use of available treatments at a less expensive cost.

As will be understood, the same holds true for skin erythema, in general.

OBJECTS OF THE PRESENT INVENTION

It is an object of the present invention, therefore, to provide an effective composition for the treatment of facial Rosacea.

It is an object of the present invention, also, to provide such a composition which is both easy to apply, and which can be obtained at a more affordable price.

It is an additional object of the invention to provide such a composition which for mild instances of Rosacea may be obtained over-the-counter, without the need for prescription.

It is a further object of the invention to provide a composition of greater concentration for a more resistant condition of Rosacea, obtainable by prescription.

SUMMARY OF THE INVENTION

As will become clear from the following description, the objects of the present invention are achieved through the employment of selenium sulfide as an active ingredient in the method of treatment of facial Rosacea. As will be understood by those skilled in the art, having the chemical formula $SS_e$, and also available as selenium disulfide $S_eS_2$, and selenium hexasulfide $S_eS_6$, selenium sulfide is an antifungal fluid agent often used in shampoos for the treatment of dandruff and seborrheic dermatitis. In such respects, selenium sulfide has been shown to be one in a class of anti-infectives that slow the growth of yeast which can lead to itching and flaking of the scalp. In a tested embodiment of the invention, selenium sulfide is combined with a cocoa butter moisturizer carrier in the treatment of the Rosacea. In a preferred embodiment, the selenium sulfide is employed as the sole active ingredient in the treatment.

As will be seen from the description and claims appended hereto, the invention stands for the propositions that:

a) No matter how virulent a condition of facial Rosacea might be, it can be treated by a one step application of a composition of only a single active agent, not a combination of them, when that single active agent is Selenium Sulfide of about 20% to about 30% of the composition; and b) The treatment for different degrees of severity of the Rosacea will be the same without having to vary any combination of active ingredients or what percentages of each are needed, when the selenium sulfide is of a 1% to 4% strength combined with a moisturizer in a lotion or cream.

In this way, a one step method of treatment can be had when the composition is left on the facial area for only 2-3 minutes.

DETAILED DESCRIPTION OF THE INVENTION

Selenium sulfide is currently employed in a concentration of 1% in such dandruff shampoos as Selsun Blue®, Exsel® lotion shampoo, Glo-Sel®, and Head & Shoulders® Intensive Treatment. It is used with warm water to be massaged as a lather into the hair and scalp, being typically used once per day, or at least two times per week as directed by the user's physician.

In accordance with the present invention, and through clinical type observations, it has been determined that a topical application utilizing selenium sulfide is effective in significantly reducing the redness, flushing and inflammation associated with the chronic, incurable adult acne-like skin condition of facial Rosacea—and with skin erythema, in general.

The composition of the invention may comprise all pharmaceutical forms for administration including solutions, gels, lotions and creams—as well as ointments, foams, emulsions, micro-emulsions, milks, serums, aerosols, sprays, dispersions, micro-capsules and micro-particles thereof. Acceptable carriers for the selenium sulfide are those suitable for topical applications for the skin, will not cause any safety or toxicity concerns, and will be compatible with the selenium sulfide. One such carrier employed successfully with the selenium sulfide has been found to be cocoa butter, an edible vegetable fat extracted from the cocoa bean. A ratio of about 3 parts cocoa butter to 1 part selenium sulfide fluid provided almost optimum results in effectiveness to decrease the erythema resulting from Rosacea. Also utilizable in soaps and cleansing bars, a fluid form selenium sulfide of 1% strength has been approved by the FDA for cover-the-counter sales—and thus more readily obtainable, and at a lesser cost than other prescription medications used to treat these skin conditions. Effective in most instances of facial Rosacea, more resistant situations can be treated by using selenium sulfide strengths of 2%, 3% or 4%; obtainable in the later percentages, however, only by way of dermatological prescription. Whether supplemented with known bases such as excipients, binders, lubricants and disintegrants—or with selected oily materials or emulsifying agents—the treatment with this composition has been noted to be effective in a simple one step application process. In fact, analysis has indicated that the composition of the invention with its use of selenium sulfide can provide similar benefits for treating other skin complaints, conditions and afflictions—as with antibacterial agents, anti-acne agents, antiparasitic agents, antifungal agents, anti-inflammatory agents, and others. As such, with the selenium sulfide, such other discreet erythema as acne and sunburn can be effectively reduced as well.

In clinical type observations, the redness, small dilated blood vessels and small red bumps characterizing the facial Rosacea have been observed to be decreased in a manner akin to the controlling of spots found on other parts of the body which appear from conditions known as Tinea Capitis (a fungal form of ringworm most commonly affecting children, causing itchy scalp and loss of hair in the affected areas) and Tinea Versicolor (a fungal itchy and scaly spotting lighter than the surrounding skin). There, fungi germs living on the tissue of the outer skin layers tend to spread easily, but whose growth is kept under reasonable control through the topical application of selenium sulfide. Treatment of dermatophyte fungal infections also with oral antifungal agents in more pronounced cases have been known to recognize the acceptance of selenium sulfide as a general preventative other than as to the specific percentages of selenium sulfide strength critical to deal with facial Rosacea, as contrasted, for example, with its general use for Tinea Versicolor proscriptions of non-use at the face and genitals.

Applicant's invention thus stands for the proposition that the skin condition known as facial Rosacea can be effectively treated with a chemical composition employing selenium sulfide as an active ingredient. More specifically, it recognizes that contra-distinct to other prior methods of treatment, a combination of several active ingredients defining the claimed combination employed with inactive ingredients is no longer required, so long as the selenium sulfide were to comprise about 20% to about 30% of the fluid composition, when a 1% to 4% strength is employed. The treatment would then effectively follow with a simple combination, where the selenium sulfide is the only active ingredient necessary, and, that more resistant folios of Rosacea could be effectively treated in this manner with increasing selenium sulfide strengths, the latter only being obtainable, however, by physician's prescription for the highest forms of the skin condition.

While there have been described what are considered to be preferred embodiments of the present invention, it will be readily appreciated by those skilled in the art that modifications can be made without departing from the scope of the teachings herein. For at least such reason, therefore, resort should be had to the claims appended hereto for a true understanding of the scope of the invention.

I claim:

1. A method of treating erythema resulting from facial Rosacea in a subject in a one step application utilizing only a single active ingredient comprising the step of topically administering to the facial area of said subject a moisturized fluid composition and leaving said moisturized fluid composition once administered for 2-3 minutes at said facial area of administration, wherein said single active ingredient of said moisturized fluid composition is selenium sulfide included to about 20% to about 30% by volume of the moisturized fluid composition as the sole active ingredient in the fluid composition for treating the erythema resulting from facial Rosacea.

2. The method of claim 1 wherein the step of topically administering to the facial area of said subject a moisturized fluid composition, topically administers to the facial area of said subject a moisturized fluid composition including selenium sulfide of 1% to 4% concentration strength.

3. A method of treating erythema resulting from facial Rosacea in a subject in a one step application comprising the step of administering topically to the face of said subject a fluid composition consisting of about 20% to about 30% by volume of selenium sulfide of a 1% to 4% concentration strength in a lotion or cream moisturizer or spray, and wherein said selenium sulfide is the sole active ingredient in the fluid composition for treating the erythema resulting from facial Rosacea.

4. The method of claim 3 wherein said fluid composition consists of a mixture of one part by volume of selenium sulfide with 3 parts by volume of cocoa butter lotion applied to the facial area of concern.

5. A method of treating erythema resulting from facial Rosacea in a subject in a one step application comprising the step of administering topically to the face of said subject a fluid composition consisting of about 20% to about 30% by volume of selenium sulfide of a 1% concentration strength in a lotion or cream moisturizer or spray, wherein said selenium sulfide is the sole active ingredient in the fluid composition for treating the erythema resulting from facial Rosacea, and wherein said selenium sulfide of about 20% to about 30% by volume in said one step application is increased from said 1% concentration strength through to a 4% concentration strength for treating the erythema resulting from increasingly resistant forms of facial Rosacea.

6. The method of claim 5 wherein said fluid composition consists of a mixture of one part by volume of selenium sulfide with 3 parts by volume of cocoa butter lotion applied to the facial area of concern.

\* \* \* \* \*